US00PP26957P2

(12) United States Plant Patent
Cullina

(10) Patent No.: US PP26,957 P2
(45) Date of Patent: Jul. 19, 2016

(54) ***ZIZIA* PLANT NAMED 'CRAZY QUILT'**

(50) Latin Name: *Zizia aptera*
Varietal Denomination: Crazy Quilt

(71) Applicant: William G. Cullina, Southport, ME (US)

(72) Inventor: William G. Cullina, Southport, ME (US)

(73) Assignee: NEW ENGLAND WILD FLOWER SOCIETY, Framingham, MA (US)

( * ) Notice: Subject to any disclaimer, the term of this patent is extended or adjusted under 35 U.S.C. 154(b) by 127 days.

(21) Appl. No.: 13/999,924

(22) Filed: Apr. 3, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

Cullina, William, "Understanding Perennials—A New Look at Old Favorites," 2009, Houghton Mifflin Harcourt Publishing Company, p. 72. (3 pages total).*

* cited by examiner

*Primary Examiner* — Susan McCormick Ewoldt
(74) *Attorney, Agent, or Firm* — Penny J. Aguirre

(57) ABSTRACT

A new cultivar of *Zizia* named 'Crazy Quilt', characterized by its heart shaped variegated foliage that changes color throughout the growing season, its spring foliage that emerges light green in color with an irregular white margin and a central dark green patch, its summer foliage that is gray-green in color with an irregular margin that is white and purple-pink in color, its fall and winter foliage that is two-toned purple and pink in color, and its small yellow umbellate flowers that emerge in the spring.

2 Drawing Sheets

Botanical classification: *Zizia aptera*.
Cultivar designation: 'Crazy Quilt'.

BACKGROUND OF THE INVENTION

The present invention relates to a new and distinct cultivar of *Zizia aptera* named 'Crazy Quilt' and is hereinafter referred to by its cultivar name 'Crazy Quilt'.

The inventor discovered the new cultivar as a naturally occurring whole plant mutation in Framingham, Mass. in spring of 2002. 'Crazy Quilt' was discovered as a single unique plant in a tray of seedlings that had been planted with seeds collected from unnamed plants of *Zizia aptera* that were grown in a cultivated area.

Asexual propagation of the new cultivar was first accomplished by the Inventor by division in Framingham, Mass. in June 2004. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Crazy Quilt' as a new and unique cultivar of *Zizia*.

1. 'Crazy Quilt' exhibits heart shaped variegated foliage that changes color throughout the growing season.
2. 'Crazy Quilt' exhibits spring foliage that emerges light green in color with an irregular white margin and a central dark green patch.

3. 'Crazy Quilt' exhibits summer foliage that is gray-green in color with an irregular margin that is white and purple-pink in color.
4. 'Crazy Quilt' exhibits fall and winter foliage that is two-toned purple and pink in color.
5. 'Crazy Quilt' exhibits small yellow umbellate flowers in the spring (similar to the species).

Plants of the parent species, *Zizia aptera*, differ from 'Crazy Quilt' in having non-variegated foliage. The flowers of 'Crazy Quilt' are not unique from the flowers of the species. There are no other cultivars of *Zizia aptera* known to the Inventor.

BRIEF DESCRIPTION OF THE DRAWING

The accompanying colored photographs illustrate the overall appearance and distinct characteristics of the new *Zizia*. The photographs were taken of a three year-old plant grown in a trail garden in Framingham, Mass.

The photograph in FIG. 1 provides a close-up view of the summer foliage of 'Crazy Quilt'.

Figure 1:
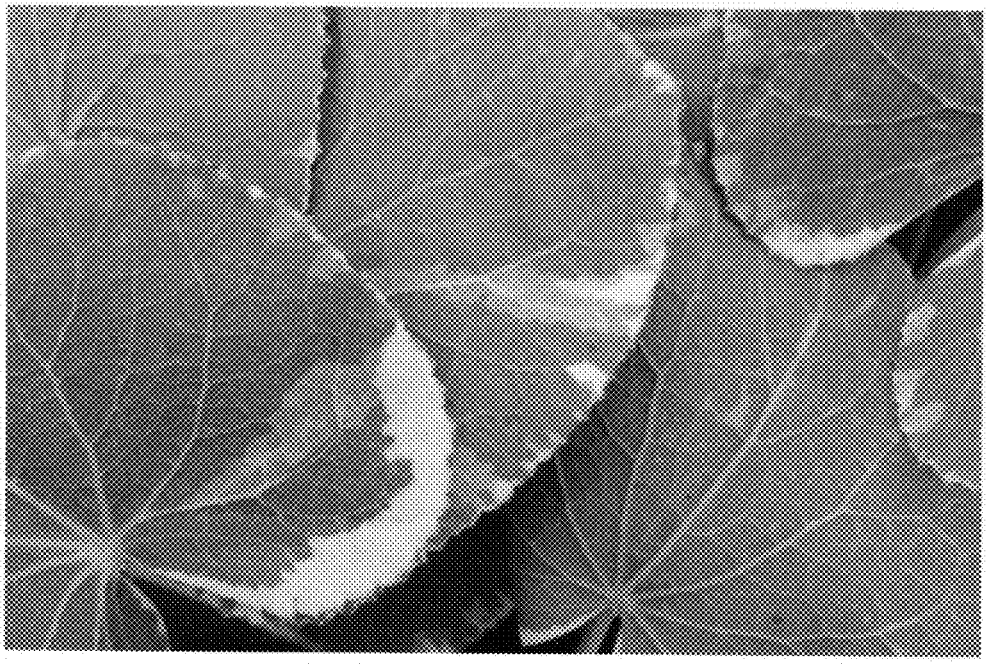
Figure 2:
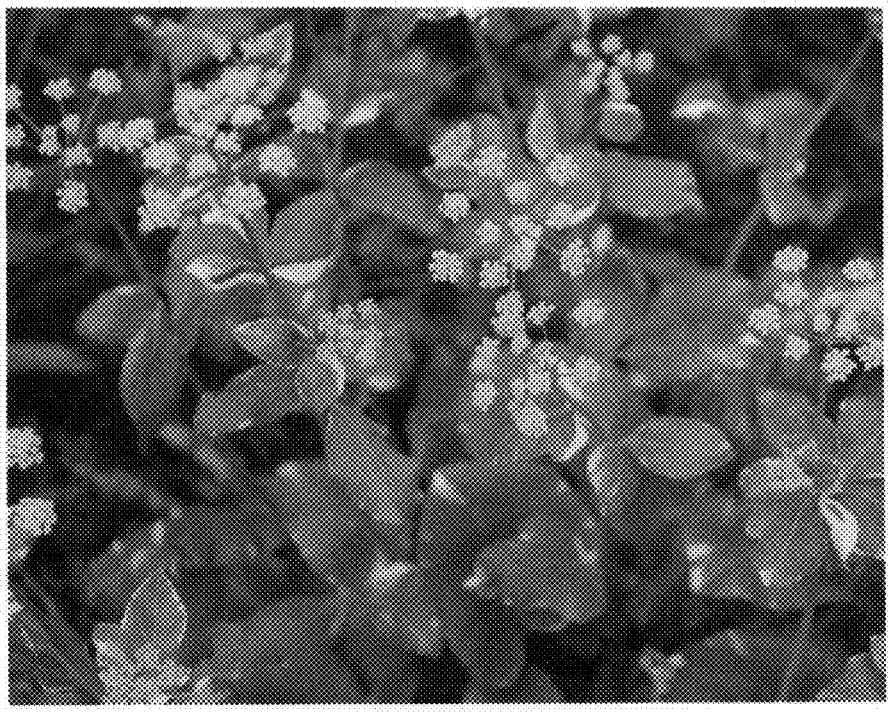

The photograph in FIG. 2 provides a view of the plant in bloom and the spring foliage of 'Crazy Quilt'.

Figure 3:
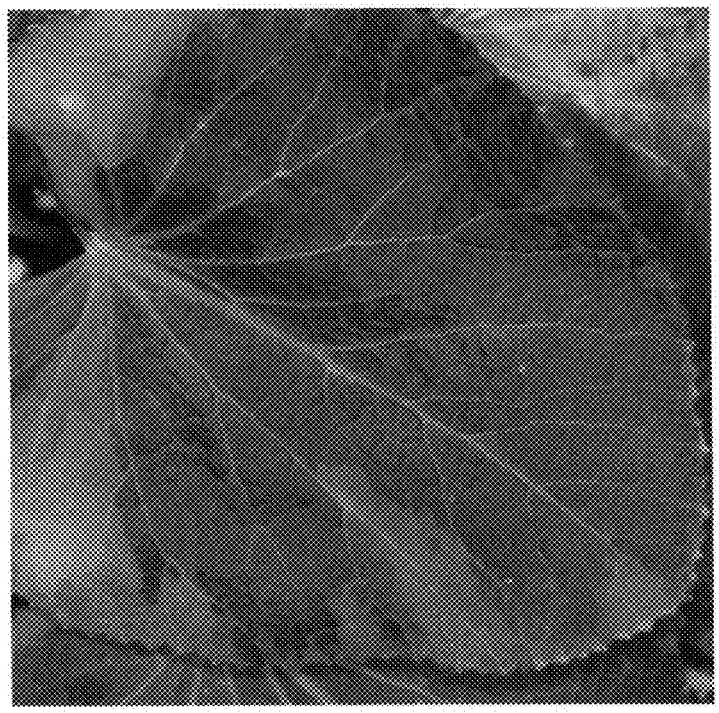

The photograph in FIG. 3 provides a view of the fall to winter foliage of 'Crazy Quilt'.

The colors in the photographs are as close as possible with the photographic and printing technology utilized and the color values cited in the detailed botanical description accurately describe the colors of the new *Zizia*.

DETAILED BOTANICAL DESCRIPTION OF THE PLANT

The following is a detailed description of three year-old plants of the new cultivar as grown outdoors in a 2-gallon container in Framingham, Mass. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Bloom period.*—Two weeks in mid to late spring in Framingham, Mass.

*Plant type.*—Herbaceous perennial.

*Plant habit.*—Compact, rosette-forming, mounded stem-less foliage, with leafy flowering stems arising above the basal foliage.

*Height and spread.*—Reaches up to 61 cm in height (measured to the top of the inflorescences) and about 41 cm in width when mature.

*Hardiness.*—At least in U.S.D.A. Zone 4.

*Diseases and pests.*—Disease free in the conditions tested, no susceptibility or resistance to pests has been observed.

*Roots.*—Stout, fleshy-fibrous, densely-packed woody rhizomes; an average of 2.5 cm in length and 1.3 cm in width, a blend of 200A and N199B in color, ridged and knotty surface.

*Propagation.*—Division and tissue culture.

*Growth rate.*—Moderate.

Stem description (flowering stems):

*Branching habit.*—Stemless, leaves emerge from rootstalk, flowering stems emerge from basal rosettes.

*Flowering stem shape.*—Oval.

*Flowering stem color.*—144B.

*Flowering stem size.*—Up to 61 cm in length and 4 mm in width.

*Flowering stem surface.*—Finely pubescent.

*Flowering stem aspect.*—Held at an average angle of 5 to 10° (0°=vertical).

Foliage description:

*Leaf shape.*—Basal leaves deltoid to cordate, cauline leaves deltoid to cordate to ternate with leaflets ovate, leaf obovate overall.

*Leaf division.*—Basal and cauline leaves simple.

*Leaf base.*—Basal leaves cordate, cauline leaves cuneate to cordate.

*Leaf apex.*—Basal and cauline leaves acute.

*Leaf venation.*—Palmate, color; 138B on upper surface and the same as leaf color on lower surface on mature leaves.

*Leaf margins.*—Basal leaves; crenate, cauline leaves; un-lobed or ternate with lobe margins crenate.

*Leaf attachment.*—Petiolate on basal and cauline leaves.

*Leaf arrangement.*—Basal leaves emerge from rootstock as a rosette, cauline leaves alternate.

*Leaf orientation.*—Basal and cauline leaves; held nearly upward from petiole.

*Leaf surface.*—Basal leaves upper surface; glabrous, dull, and coriaceous, basal leaves lower surface; very finely puberulent, cauline leaves upper and lower surface; glabrous and dull.

*Leaf color.*—Spring upper and lower surface; 146B with irregular margin markings of 158B, summer upper surface; a blend between N137C and 189A with irregular markings of 158B and margins 186A, summer lower surface; 191A with irregular margin markings of 158B and margins 186A, fall and into winter upper and lower surface; centers 79A with irregular margins of 67A.

*Leaf size.*—Basal leaves; emerge small; an average of 1.2 cm in length and 1.5 cm in width gradually becoming larger to range from 3 to 10 cm in length and 7 cm in width, cauline leaves; an average of 3 cm in length and diameter with lobes an average of 2 cm in length and 1.5 cm in width when ternate.

*Leaf quantity.*—Basal leaves; about 5 per rootstock, about 30 densely packed rootstock as grown in a 2-gallon container, cauline leaves; an average of 3 per flowering stem.

*Petioles.*—Basal leaves; oval in shape, average of 13 cm in length and 2 mm in width on mature leaves, 138B in color on mature leaves, surface is pubescent with very short stiff hairs, base is winged with wings about 1 cm in length and 1 mm in width, translucent and 145C in color, cauline leaves; an average of 1 cm in length and 2.5 mm in width, 144B in color, very lightly pubescent surface.

Flower description:

*Inflorescence type.*—Compound umbel, 1 to 3 per stem.

*Inflorescence size.*—An average of 8 cm in height and about 10 cm in width.

*Inflorescence number.*—An average of 12 per three year-old plant.

*Flower fragrance.*—None.

*Flower quantity.*—Average of 140 flowers per flowering stem.

*Flower lastingness.*—Average of two weeks.

*Flower buds.*—Globose in shape, an average of 1.5 mm in diameter and 3 mm in depth, apex is 1B in color with calyx portion 144A.

*Flower aspect.*—Upright and outward.

*Flower type.*—Campanulate with petals recurved inward.

*Flower size.*—About 3 mm in length and 1.5 mm in diameter.

*Petals.*—5, oval in shape, and average of 1.5 mm in length and 1.5 mm in width margin is entire, apex is obtuse and curled inward, base is truncate, upper and lower surface 1A in color.

*Calyx.*—Comprised on 5 fused sepals, oval in shape, average of 2 mm in depth and diameter, outer and inner surface 145A in color with glabrous surface.

*Peduncles.*—Average of 1.4 cm in length and 1 mm in width, glabrous surface, held upright to horizontal, color a blend of 138B and 138C.

*Pedicels.*—Average of 1 mm in length and 0.7 mm in width, color a blend of 138B and 138C, surface glabrous.

Reproductive organs:

*Gynoecium.*—1 pistil, stigmas bifid and 145B and translucent in color, styles are about 1 mm in length and 145D in color, ovaries are 144A in color.

*Androcoecium.*—5 stamens, anthers are about 0.7 mm in length and 0.5 mm in width, in color, filament 1 mm in length and 145D in color, pollen was not observed.

*Seed/fruit.*—Fruit; oblong to ovate shizocarp, an average of 3 mm in length, laterally flattened with 5 unwinged ribs along each carpel, N186A in color.

It is claimed:

1. A new and distinct cultivar of *Zizia aptera* plant named 'Crazy Quilt' as herein illustrated and described.

* * * * *